United States Patent
Della Santina et al.

(10) Patent No.: US 7,647,120 B2
(45) Date of Patent: *Jan. 12, 2010

(54) DUAL COCHLEAR/VESTIBULAR STIMULATOR WITH CONTROL SIGNALS DERIVED FROM MOTION AND SPEECH SIGNALS

(75) Inventors: Charles C. Della Santina, Towson, MD (US); Michael A. Faltys, Northridge, CA (US)

(73) Assignees: John Hopkins School of Medicine, Baltimore, MD (US); Advanced Bionics, LLC, Valencia, CA (US)

( * ) Notice: Subject to any disclaimer, the term of this patent is extended or adjusted under 35 U.S.C. 154(b) by 315 days.

This patent is subject to a terminal disclaimer.

(21) Appl. No.: 11/744,640

(22) Filed: May 4, 2007

(65) Prior Publication Data
US 2007/0208403 A1    Sep. 6, 2007

Related U.S. Application Data

(63) Continuation-in-part of application No. 11/134,658, filed on May 20, 2005, now Pat. No. 7,225,028.

(60) Provisional application No. 60/575,615, filed on May 28, 2004.

(51) Int. Cl.
*A61N 1/18*     (2006.01)
(52) U.S. Cl. .................. 607/57; 600/379; 607/55; 607/56; 607/60
(58) Field of Classification Search .......... 600/379, 600/559; 607/55–60, 62, 65, 72, 116, 136, 607/137
See application file for complete search history.

(56) References Cited

U.S. PATENT DOCUMENTS

| | | | |
|---|---|---|---|
| 3,942,535 A | 3/1976 | Schulman | |
| 4,495,917 A | 1/1985 | Byers | |
| 4,516,820 A | 5/1985 | Kuzma | |
| 4,532,930 A | 8/1985 | Crosby et al. | |
| 4,592,359 A | 6/1986 | Galbraith | |
| 4,764,132 A | 8/1988 | Stutz, Jr. | |
| 4,947,844 A | 8/1990 | McDermott | |
| 5,601,617 A | 2/1997 | Loeb et al. | |
| 5,626,629 A | 5/1997 | Faltys et al. | |
| 5,711,308 A * | 1/1998 | Singer .................. | 600/559 |
| 5,776,172 A | 7/1998 | Schulman et al. | |
| 5,876,425 A | 3/1999 | Gord et al. | |
| 5,919,149 A | 7/1999 | Allum | |
| 6,002,966 A | 12/1999 | Loeb et al. | |
| 6,063,046 A | 5/2000 | Allum | |
| 6,067,474 A | 5/2000 | Schulman et al. | |

(Continued)

FOREIGN PATENT DOCUMENTS

EP    1449561 A1    3/2001

(Continued)

*Primary Examiner*—Carl H Layno
*Assistant Examiner*—Erica Lee
(74) *Attorney, Agent, or Firm*—Victoria A. Poissant; Bryant R. Gold

(57) ABSTRACT

A system for treating patients affected both by hearing loss and by balance disorders related to vestibular hypofunction and/or malfunction, which includes sensors of sound and head movement, processing circuitry, a power source, and an implantable electrical stimulator capable of stimulating areas of the cochlea and areas of the vestibular system.

14 Claims, 7 Drawing Sheets

U.S. PATENT DOCUMENTS

| | | | |
|---|---|---|---|
| 6,157,861 A | 12/2000 | Faltys et al. |
| 6,219,578 B1 | 4/2001 | Collins et al. |
| 6,219,580 B1 | 4/2001 | Faltys et al. |
| 6,272,382 B1 | 8/2001 | Faltys et al. |
| 6,289,247 B1 | 9/2001 | Faltys et al. |
| 6,376,771 B1 | 4/2002 | Kosuge |
| 6,487,453 B1 | 11/2002 | Kuzma et al. |
| 6,546,291 B2 | 4/2003 | Merfeld et al. |
| 6,826,430 B2 | 11/2004 | Faltys et al. |
| 6,842,647 B1 | 1/2005 | Griffith et al. |
| 6,980,864 B2 | 12/2005 | Faltys et al. |
| 7,039,466 B1 | 5/2006 | Harrison et al. |
| 7,043,304 B1 | 5/2006 | Griffith et al. |
| 7,054,691 B1 | 5/2006 | Kuzma et al. |
| 7,076,308 B1 | 7/2006 | Overstreet et al. |
| 7,092,763 B1 | 8/2006 | Griffith et al. |
| 7,107,101 B1 | 9/2006 | Faltys |
| 7,225,028 B2 * | 5/2007 | Della Santina et al. | 607/57 |
| 2003/0036782 A1 | 2/2003 | Hartley et al. |
| 2004/0044383 A1 | 3/2004 | Woods et al. |
| 2005/0245991 A1 | 11/2005 | Faltys et al. |
| 2005/0251225 A1 | 11/2005 | Faltys et al. |

FOREIGN PATENT DOCUMENTS

| | | |
|---|---|---|
| WO | WO 03/030772 A2 | 4/2003 |

* cited by examiner

DUAL COCHLEAR/VESTIBULAR STIMULATOR WITH CONTROL SIGNALS DERIVED FROM MOTION AND SPEECH SIGNALS

The present application is a Continuation-in-part of U.S. patent application Ser. No. 11/134,658, filed May 20, 2005, now U.S. Pat. No. 7,225,028; which claims the benefit of U.S. Provisional Patent Application Ser. No. 60/575,615, filed May 28, 2004, which applications are incorporated herein by reference.

FIELD OF THE INVENTION

The present invention relates to cochlear implant systems and methods, and more particularly relates to a system for treating patients suffering from deficiencies of both cochlear and vestibular labyrinthine (balance) function.

BACKGROUND OF THE INVENTION

For patients with both cochlear and vestibular sensory loss, a hybrid cochlear/vestibular implant offers significant advantages over single modality prostheses that address only cochlear or only vestibular function. Cochlear and vestibular sensory loss frequently occur together, because hair cells in both parts of the inner ear are similarly sensitive to ototoxic drug exposure, Ménière's disease, infection, trauma, genetic defects and other diseases. Currently available cochlear implants (e.g., in U.S. Pat. Nos. 4,532,930; 4,592,359; 4,947,844; 5,776,172; and 6,067,474) can restore auditory sensation, and a single-modality vestibular prosthesis (e.g., in U.S. Pat. No. 6,546,291) can provide artificial vestibular sensation; however, patients with combined loss of hearing and vestibular sensation currently have no effective therapeutic options. While disability due to loss of vestibular sensation varies widely, patients may be severely affected by chronic disequilibrium and oscillopsia (visual field movement during head movements) that impede activities of daily life. The vestibular nerve should be intact in most cochlear implantation candidates with loss of vestibular sensation. In these patients, a hybrid cochlear/vestibular implant can selectively stimulate all branches of the auditory-vestibular (eighth cranial) nerve, restoring hearing and normalizing gaze- and posture-stabilizing reflexes and perception of spatial orientation.

Presently available implantable stimulation devices, such as a cochlear implant device or a neural stimulator, typically have an implanted unit, an external ac coil, and an external control unit and power source. The external control unit and power source includes a suitable control processor and other circuitry that generates and sends the appropriate command and power signals to the implanted unit to enable it to carry out its intended function. The external control unit and power source are powered by a battery that supplies electrical power through the ac coil to the implanted unit via inductive coupling for providing power for any necessary signal processing and control circuitry and for electrically stimulating select nerves or muscles. Efficient power transmission through a patient's skin from the external unit to the implanted unit via inductive coupling requires constant close alignment between the two units.

Representative prior art cochlear implant systems are disclosed, e.g., in U.S. Pat. Nos. 4,532,930; 4,592,359; 4,947,844; 5,776,172; and 6,067,474; all of which are incorporated herein by reference in their entireties.

Disadvantageously, each of the known prior art cochlear stimulation systems requires the use of an external power source and speech processing system, coupled to the implanted stimulation device. For many patients, achieving and maintaining the required coupling between the external components and the implanted component can be troublesome, inconvenient, and unsightly. Thus, there existed a need and desire for a small, lightweight fully implantable device or system that does not require an external unit in order to be fully functional, that does not need constant external power, and that includes a long-lasting internal battery that may be recharged, when necessary, within a relatively short time period.

This and other needs were satisfied by the development of fully implantable cochlear implant systems such as that disclosed by U.S. Pat. No. 6,272,382, incorporated herein by reference in its entirety. A fully implantable cochlear implant system includes at least three main modules, including (1) a small implantable cochlear stimulator (ICS) module, with permanently attached cochlear electrode array; (2) an implantable speech processor (ISP) module, with integrated microphone and rechargeable battery; and (3) an external module.

All of the prior art cochlear implant systems currently available provide significant benefits to patients who wish to hear. A significant percentage of these patients implanted with cochlear stimulation systems suffer from balance deficiencies originating in the vestibular system. Recently, others have attempted to treat balance deficiencies through a variety of different modalities, including stimulating the vestibular system. Representative vestibular stimulation systems are taught in U.S. Pat. Nos. 6,546,291 (the '291 patent); 6,219,578 (the '578 patent); 6,063,046 (the '046 patent); and 5,919,149 (the '149 patent); all of which are incorporated herein by reference in their entireties.

In the '291 patent issued on Apr. 8, 2003, Merfeld, et al. teach a balance prosthesis that provides information indicative of a patient's spatial orientation to the patient's nervous system. This is done by placing 3 rotational accelerometers in mutually orthogonal cardinal X Y and Z planes to measure roll, pitch and yaw of the head (see, '291 Merfeld patent at column 4 line 35). In the '578 patent issued on Apr. 17, 2001, Collins, et al. teach transcutaneous electrical stimulation of the vestibular system in order to modify a patient's postural sway. In the '046 patent issued on May 16, 2000, Allum teaches a method and apparatus for the diagnosis and rehabilitation of abnormal human balance corrections. And, in the '149 patent issued on Jul. 6, 1999, Allum teaches a method and apparatus for the diagnosis and rehabilitation of abnormal human postural sway.

As exemplified above, there are systems for treating hearing deficiencies and balance deficiencies separately. However, there is no single system currently available for simultaneously treating patients with both hearing and balance deficiencies. Therefore, a need exists for an invention that treats cochlear implant patients affected by balance disorders related to vestibular hypofunction and malfunction.

BRIEF SUMMARY OF THE INVENTION

The teachings of the present disclosure solves the above and other needs by providing systems and methods capable of simultaneously enabling both auditory and vestibular sensation in patients with combined deafness and vestibular hypofunction. The present disclosure incorporates all of the teachings of the prior art cochlear implant and vestibular stimulation systems exemplified by the patents previously discussed and incorporated herein by reference to provide a hybrid cochlear/vestibular implantable stimulator. The present disclosure encompasses the novel idea of a hybrid cochlear/vestibular stimulator capable of alleviating the symptoms of cochlear implant candidates affected by balance disorders related to vestibular hypofunction. The hybrid stimulator of the present disclosure provides vestibular stimulation for the purpose of providing spatial information, such as rotational and translational acceleration, velocity and/or position of the head or body and an estimate of the gravity vector, to a patient's cochlea and vestibular system.

In one embodiment of the present disclosure, a cochlear prosthesis, such as a fully implantable cochlear stimulator, is enhanced with a spatial orientation devices such as rotational and linear accelerometers. Signals from these sensors are encoded into stimuli by the hybrid cochlear/vestibular prosthesis signal processor and are presented to the vestibular system by at least one electrode array. The electrode array is preferably independent from the intra-cochlear array. The electrical signals sent to the vestibular system selectively stimulate portions of the vestibular nerve to emulate activity that normally occurs with physiologic stimulation of the three semicircular canals and two otolith sensors, thus providing rotation and orientation information to the patient's brain. Alternatively, electrical stimuli may be presented directly to the sensory epithelia of the canals and otolith sensors, or to vestibular nuclei in the central nervous system.

The sensor(s) and the signal processor(s) of the present disclosure may either be fully implanted or implemented outside the body. If implemented outside the body of a patient, both stimulation signals and power must be transmitted in to the implanted portions of the systems of the present disclosure.

A method of the present disclosure may include stimulating the vestibular system independent of the cochlear system by means of a microstimulator. The microstimulator may include one or more electrodes or may additionally or alternatively include a lead attached to the microstimulator. The electrode(s) of the microstimulator may be placed next to nervous tissue of the vestibular sensory system.

BRIEF DESCRIPTION OF THE DRAWINGS

The above and other aspects of the present disclosure will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Overview

One embodiment of the present disclosure relates to an implantable cochlear/vestibular stimulation system that is partitioned into two components: (1) a hybrid cochlear/vestibular stimulator component and associated electrode array(s) which are designed to last for the life of the patient; and (2) an implantable speech/motion processor and battery component which are designed to be explanted and replaced from time to time. It is to be understood, however, that other embodiments of the disclosure may be used. For example, the present disclosure may be practiced in a single implantable component, which comprises a fully implantable cochlear/vestibular stimulation system. It is also to be understood that the present disclosure need not be limited to just a fully implantable cochlear/vestibular stimulation system. Any medical or other device or system which is implanted in living tissue near the cochlear and/or vestibular systems, or a similar environment, and which requires operating power from a replenishable power source, such as a rechargeable battery, and wherein the operating power is inductively or magnetically or otherwise coupled into the implantable device without a direct electrical connection, may benefit from the application and teachings of the present disclosure.

Figure 1A:
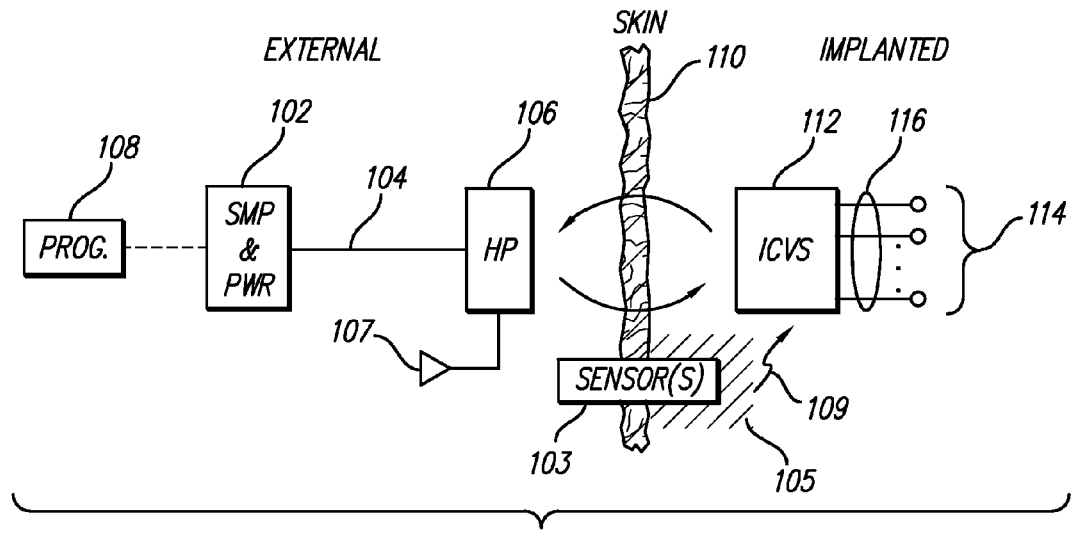
FIG. 1A illustrates an exemplary embodiment of a hybrid cochlear/vestibular stimulation system, including an implantable cochlear/vestibular stimulator (ICVS) that is inductively (or otherwise) coupled with an external headpiece (HP) connected with a speech and motion processor (SMP), motion sensor(s), and power source.

To better understand and appreciate the teachings of the present disclosure, it will be helpful to briefly review current or existing cochlear stimulation systems, which are generally representative of all tissue-stimulating systems. A representative cochlear stimulation system of the type currently used by many patients is fully described, e.g., in U.S. Pat. No. 5,776,172 previously referenced and incorporated herein by reference. Some of the components of the '172 patent are illustrated in FIG. 1A in combination with other novel elements of the present disclosure. The system shown in FIG. 1A includes implanted and external components. The external components include a speech and motion processor (SMP), a power source (e.g., a replaceable battery), a headpiece (HP) 106, and at least one orientation/motion sensor 103. The sensor(s) 103 is (are) preferably fixed with respect to the skull, hence FIG. 1A shows the sensor(s) 103 at least partially embedded in or affixed to the bone 105 of the skull. Thus, e.g., in one embodiment, the sensor(s) 103 are fully implanted, and thus remain fixed with respect to the skull. In another embodiment, the sensor(s) 103 may be external, but are rigidly fixed to the skull using, e.g., a transcutaneous osseointegrated implant such as those employed to affix bone-anchored hearing aids. It should also be noted that the motion sensor processor, although shown in FIG. 1A as an external component (part of the SMP 102), may instead be an implanted component (part of the ICVS 112), in which case signals from the sensor(s) 103 may be sent to the ICVS 112 via an RF or other suitable wireless link 109. At least the speech processor and power source (and in some embodiments the motion processor) may be housed within a wearable unit 102 that is worn or carried by the patient. The wearable unit is electrically connected to the HP 106 via a cable 104. A microphone 107 is also included as part of the headpiece 106.

The implanted components include an implantable cochlear/vestibular stimulator (ICVS) 112, embedded motion sensors 105 (in some embodiments), and an array of electrodes 114. The electrode array 114 is intended for implantation within the cochlea of the patient and within or near neural tissue of the vestibular system. Neural vestibular tissue that may be stimulated by the electrical stimulation pulses generated by the ICVS 112 includes at least the sensory epithelium of the vestibular end organs; the vestibular nerve; the semicircular canals; the nerve fiber bundles that separately serve each one of the five end organs in each inner ear; the vestibular branch of the eighth nerve, or Scarpa's ganglion; the vestibular afferents; the vestibular nuclei of the brain stem; any portion of the central nervous system through which it is possible to elicit a vestibular response, reflex, or sensation; or on the surface of the skin near one or more of the foregoing stimulation sites. The ICVS 112 is implanted behind the ear, so as to reside near the scalp. The electrode array 114 is permanently connected to the ICVS by way of a multi-conductor implantable cable 116.

Multiple electrode arrays 114 may be employed by the present disclosure. In one such an embodiment, the ICVS 112 has at least two channels and preferably sufficient channels to be able to produce monopolar or bipolar stimulation to preferably at least three separate electrode arrays implanted near ampullary branches of the vestibular nerve and two or more otolith endorgan branches. For example, the ICVS 112 could include two electrode arrays 114, one of which is configured to stimulate the cochlea, the other of which is trifurcated at its end (i.e., has three separate branches including at least one electrode on each branch) so that each of its three branches can be separately implanted within a different semicircular canal ampulla of the vestibular system, or alongside the ampullary nerves, to encode rotational motion. Similarly, additional branches of the electrode's array may be implanted near the otolith endorgans or the branches of the vestibular nerve that innervate them, to encode linear acceleration.

Inside of the headpiece 106 is a coil that is used to inductively or magnetically couple a modulated AC carrier signal to a similar coil that is included within the ICVS 112. In order to achieve efficient coupling, without suffering significant losses in the signal energy, it is important that the external coil within the headpiece be properly aligned with the internal coil inside the ICVS 112. To achieve proper alignment, a magnet is typically included within both the headpiece 106 and the ICVS 112, and the resulting magnetic attraction between the two magnets not only aligns the coils, as desired, but also provides a holding force that maintains the headpiece 106 securely against the scalp or skin 110 of the patient. Disadvantageously, the use of such a magnet may, for some patients, limit their ability to have magnetic resonance imaging (MRI) performed on them, at least in the vicinity of the head. However, the magnet may be temporarily removed when an MRI is required.

In use, a carrier signal is generated by circuitry within the wearable unit 102 using energy derived from the power source within the speech processor unit 102. Such carrier signal, which is an AC signal, is conveyed over the cable to the headpiece 106 where it is inductively coupled to the coil within the ICVS 112. There it is rectified and filtered and provides a DC power source for operation of the circuitry within the ICVS 112. Sounds are sensed through the microphone 107 and movements, gravity, and orientation are sensed through the motion sensors 103. The motion sensors 103 are preferably rigidly fixed to the skull. Such rigid fixation, as indicated previously, may be achieved by embedding the sensors 103 to the bone 105 of the skull, or by implanting the sensors 103, e.g., the sensors 103 may be fixed to the case of the ICVS 112. The information sensed by the microphone 107 and sensors 103 is processed by circuitry included within the speech processor unit 102 and/or the ICVS 112, and converted to appropriate stimulation signals in accordance with a selected speech and motion processing strategy by circuitry within the SMP processor unit 102 or ICVS 112. These stimulation signals modulate the carrier signal that transfers power to the ICVS 112. The ICVS includes an appropriate demodulation circuit that recovers the stimulation signals from the modulated carrier and applies them to the electrodes within the electrode array 114. The stimulation signals identify which electrodes, or electrode pairs, are to be stimulated, the sequence of stimulation and the intensity of the stimulation.

Some embodiments of the ICVS 112, as indicated in the '172 patent, include a back telemetry feature that allows data signals to be transmitted from the ICVS 112 to the headpiece 106, and hence to the speech and motion processor 102. Such back telemetry data provides important feedback information to the speech and motion processor regarding the operation of the ICVS, including the amount of power needed by the ICVS. See, e.g., U.S. Pat. No. 5,876,425, issued to the same assignee as the present application, and also incorporated herein by reference.

When adjustment or fitting or other diagnostic routines need to be carried out, an external programming unit 108 is detachably connected to the SMP unit 102. Through use of the external programmer 108, a clinician, or other medical personnel, is able to select the best speech and motion processing strategies for the patient, as well as set other variables associated with the stimulation process. See, e.g., U.S. Pat. No. 5,626,629 incorporated herein by reference, for a more detailed description of a representative speech fitting/diagnostic process and U.S. Pat. Nos. 6,546,291; 6,219,578; 6,063,046; and 5,919,149 all incorporated herein by reference, for a more detailed description of representative motion fitting/diagnostic processes.

Although the system shown in FIG. 1A has been of great value and benefit to many patients who could not otherwise experience the sensation of hearing, there are several drawbacks associated with use of the system. For example, the wearable unit 102 must be worn or carried by the patient, and the cable 104, which may be up to one meter long, must be routed from the unit 102 to the headpiece 106. Some patients find wearing the unit 102 to be inconvenient, and find the use of the headpiece 106, with its cable 104, to be unsightly and uncomfortable.

Figure 1B:
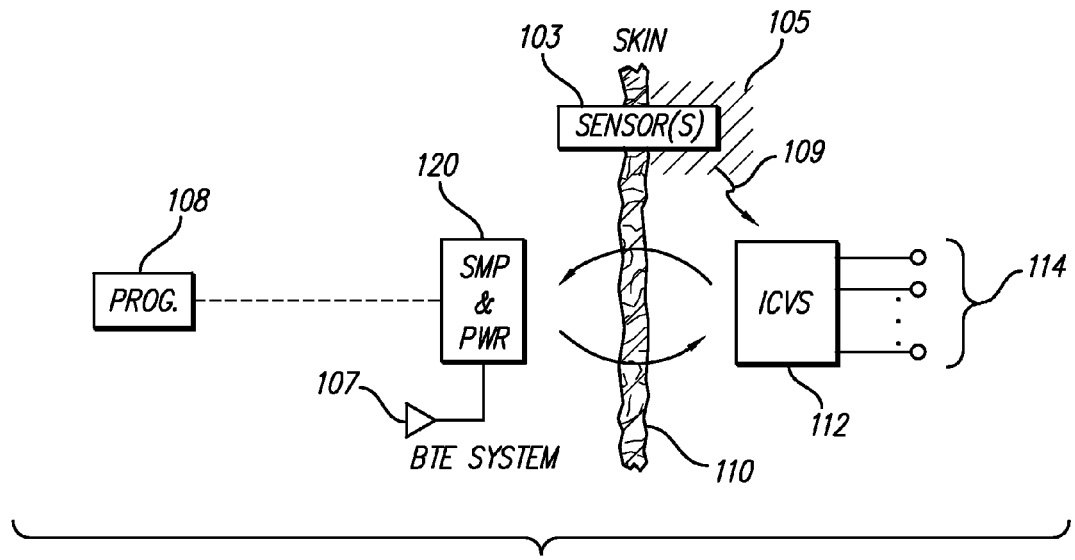
FIG. 1B illustrates another exemplary embodiment of a hybrid cochlear/vestibular stimulation system, namely a behind-the-ear (BTE) cochlear/vestibular stimulation system that includes an implanted cochlear/vestibular stimulator (ICVS) and an external BTE unit that includes a power source, a speech and motion processor, motion sensor(s), and a microphone.

In order to eliminate the need for the cable 104, a behind-the-ear (BTE) unit 120 has been proposed, as illustrated in FIG. 1B. The BTE unit 120 may include everything that was previously included within the wearable unit 102, only in a much smaller volume. The BTE unit 120 thus includes a suitable power source, as well as the circuitry needed for performing desired speech and motion processing functions. With the BTE unit 120, there is thus no need for the cable 104, and the patient simply wears the BTE unit behind his or her ear, where it is hardly noticed, especially if the patient has hair to cover the BTE unit.

Advantageously, the batteries employed within the wearable unit 102 (FIG. 1A) or the BTE unit 120 (FIG. 1B) may be readily replaced when needed. Still, the BTE unit 120 may become uncomfortable to wear when worn for long periods of time, and must be removed at certain times, such as when swimming or bathing. When the BTE unit 120 is removed, the cochlear/vestibular stimulation will cease and the patient will be unable to hear and or balance herself properly. Some patients would thus like the convenience of being able to hear at all times, including when swimming or bathing. Further, patients may become severely disoriented or experience extreme vertigo and loss of balance without power as typically supplied by the BTE unit 120. Thus, a fully implantable stimulation system, or a system with at least the vestibular portion fully implanted, is desired.

Thus, one embodiment of the present disclosure is also directed to fully implantable devices and systems that employ a rechargeable battery or other replenishable power source similar to those disclosed in U.S. Pat. Nos. 3,942,535 and 6,272,382.

Advantageously, different implant configurations may be used as part of the fully implantable system, including, in one embodiment, the ability to use the ICVS 112 in a fully implantable system.

Figure 1C:
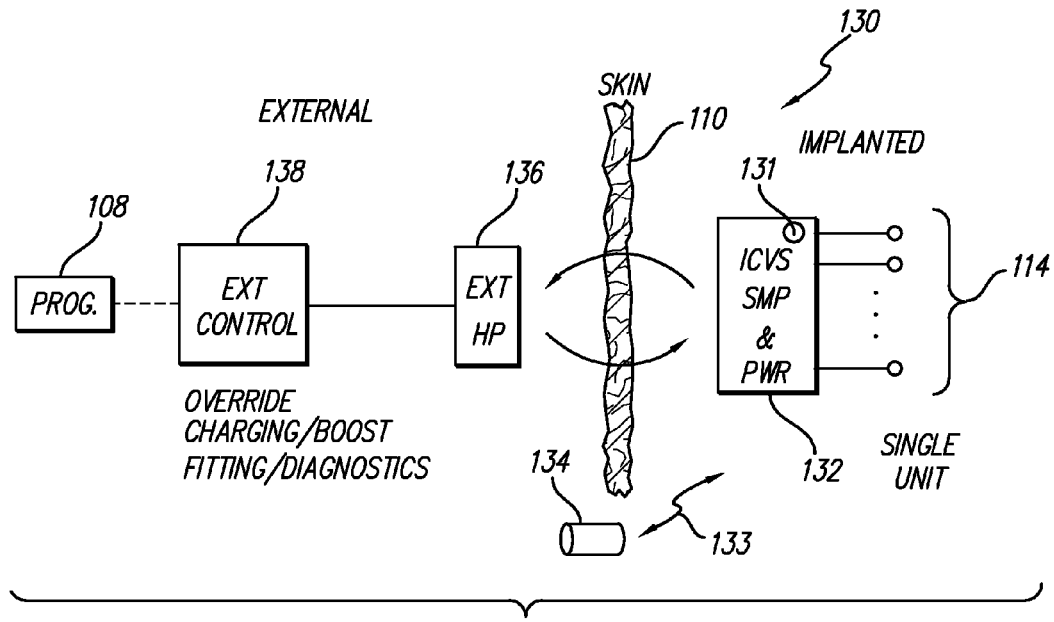
FIG. 1C shows yet another exemplary embodiment of a hybrid cochlear/vestibular stimulation system, wherein one type of a single unit, i.e., a fully implantable cochlear/vestibular stimulation system, is used.

One embodiment of a fully implantable single component system 130 is shown in FIG. 1C.

As illustrated in FIG. 1C, such system 130 includes the ICVS circuitry, the speech and motion processor (SMP) circuitry, and a power source (PWR) within a single unit 132. As explained in the systems above, at least one electrode array 114 is connected to the single unit 132 in conventional manner. For the embodiment shown in FIG. 1C, a microphone 134 is coupled via a telecoil link, or similar wireless link, which link is represented by the wavy arrow 133, to the single unit 132. Such telecoil or other wireless link powers the microphone circuits through magnetic coupling from the unit 132. Sounds sensed by the microphone 134 are transmitted to the unit 132 via an RF transmitter built-in to the microphone 134. (The transmission distance for such signal is very short, only a centimeter or two, so not much power is needed for such transmission.) Advantageously, such microphone 134 may be inserted inside the ear canal so it is not visible externally.

Other types of microphones may also be used with the implant unit 132. For example, externally generated sound waves may be sensed through the patient's skin and case shell or wall of the single unit 132 at locations where the case shell or wall is properly supported and of the proper thickness. An example of an implantable microphone is described in U.S. Pat. No. 6,376,771, incorporated herein by reference.

Motion, movement, gravity, and/or orientation sensors 131, like sensors 103, are included within the unit 132, or are mounted to the case of the unit 132. All sensors of the present disclosure include translation and rotation sensors oriented to sense a patient's roll, pitch and yaw as described in the '291 patent. In contrast to the sensor's described in the '291 patent, however, which sensors require the placement of three rotational accelerometers in mutually orthogonal cardinal X Y and Z planes to measure roll, pitch and yaw of the head, the rotational sensors in the present device may be aligned with the semicircular canal planes of the implanted patient (measured via CT scan) or mean human semicircular planes (measured with respect to skull landmarks). The desired sensing can be approximately achieved by rotating the roll/pitch/yaw oriented sensors 45 degrees in yaw and then 20 degrees pitch nose-up with respect to the head. This refinement improves the computational efficiency of the device (and can thus reduce the power consumption), by obviating the need to perform a 3×3 matrix multiplication to computationally determine the roll, pitch and yaw. In the preferred embodiment, the motion processor retains the ability to perform this computation if required to account for misalignment of the sensors.

Lightweight accelerometers, discussed, e.g., in the '578 patent and lightweight body sway sensors, such as velocity transducers or sensors as described throughout the '046 and '149 patents, may also be used or included as part of the sensors 131. In addition, micro-electro-mechanical systems (MEMS) accelerometers, piezo-electric accelerometers, or other rotation and/or linear accelerometers may be used.

Motion or other sensors of the present disclosure not located within the body may include those discussed by the patents incorporated herein by reference, including the EMG electrodes of the '046 patent. In all embodiments, motion sensors 131 may be replaced and/or accompanied by externally worn motion sensors. Where externally worn motion sensors are used, the data sensed from such sensors may be transmitted to implanted SMPs or motion processors (MPs) via an external headpiece. See, e.g., headpiece 136 of FIGS. 1C-1E.

When the battery included within the single unit 132 needs to be recharged, which may only be a few minutes a day, or a few times during the week, an external headpiece 136 is placed adjacent the unit 132, and inductive coupling is used to transfer charging power to the unit's battery. The external headpiece, in turn, connects to an external control unit 138, which may, in turn, derive its power from replaceable batteries or from an AC power plug. When programming and/or diagnostic tests are needed, an external programmer 108 may be detachably connected to the external control unit 138.

The external control unit 138 may thus be used to charge/recharge the battery within the implanted unit 132, as well as for other purposes. For example, the external control unit 138 may be used to override the internal speech and motion processor with an external speech and motion processor, e.g., a speech and motion processor included within the external programmer 108. Further, the external control unit 138 may be used to boost the power provided by the internal battery. The external control unit 138 may also be used for programming the implant device 132, e.g., fitting the ICVS after implant or adjusting the stimulation parameters of the fully implantable unit 132, as well as for diagnostic purposes.

For the embodiment 130 shown in FIG. 1C, as well as for the other embodiments shown in FIGS. 1D and 1E, discussed below, it is to be understood that back telemetry may be employed to allow data signals to be sent from the implanted unit to the external headpiece 136, and hence to the external control unit 138.

Figure 1D:
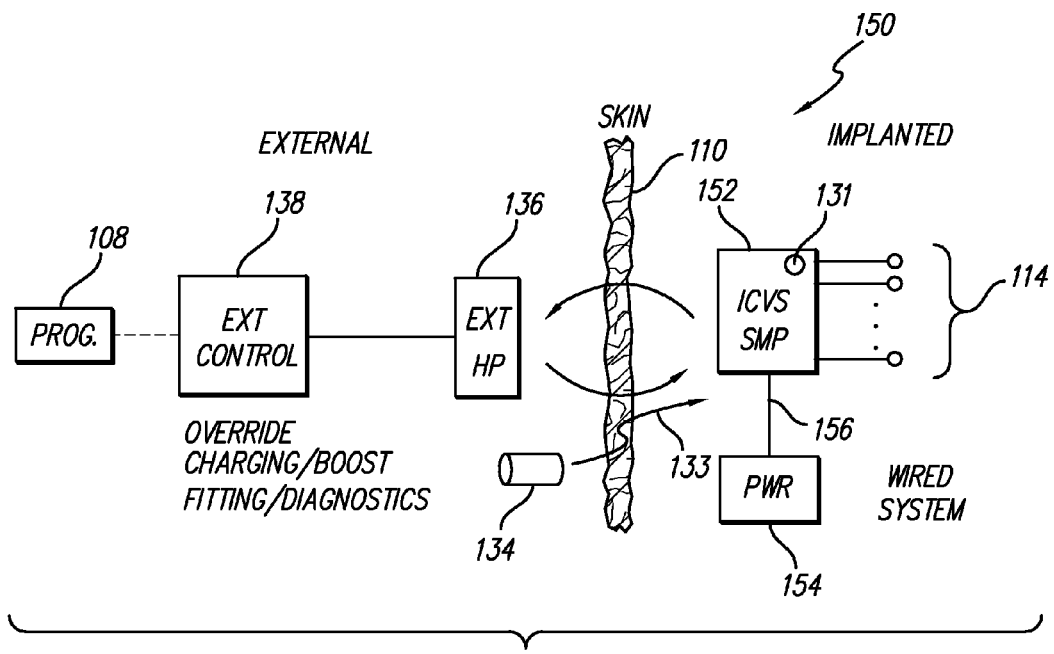
FIG. 1D shows still another exemplary embodiment of a hybrid cochlear/vestibular stimulation system, wherein a fully implantable, partitioned, wired system is utilized.

Turning next to FIG. 1D, a "wired system" embodiment 150 of the disclosure is depicted. In such wired system 150, at least two separate implantable units 152 and 154 are employed and the circuits of the system are partitioned between the two units. In a first unit 152, for example, speech and motion processor (SMP) circuitry, ICVS circuitry, and motion sensors 131 are housed, and such unit is permanently connected to an electrode array 114. In a second unit 154, a battery, or other suitable power source, is housed. The second unit 154 is electrically connected to the first unit 152 via a detachable cable 156. Other embodiments of the partitioned system may, as explained below, place the ICVS circuitry in one unit, and one or more portions of the SMP and/or the battery in another unit or units. Still other embodiments may divide the functions of the ICVS into separate components of an implantable cochlear stimulator (ICS) and an implantable vestibular stimulator (IVS), which ICS and IVS may be placed in separate implanted units, which either communicate with each other and/or communicate with other implanted components of the present disclosure.

Preferably, only AC power should be coupled from the power unit 154 to the other unit 152, thereby preventing any possibility that a DC current might flow through the tissue through which the cable is routed. This is important because a DC current could cause damage to the tissue, whereas an AC current is less likely to do so. Also, because the cable is not hermetically insulated from the surrounding tissue, minor leakage current could flow through the tissue if it carried DC currents.

The unit 154 includes appropriate switching circuitry that converts the DC power associated with the battery (or other power storage element) therein to an AC signal for coupling to the first unit 152. Also, appropriate circuitry is employed to allow AC power induced into the unit 152 from the external headpiece 136 to be directed to the battery in the unit 154 in order to charge the battery.

A representative power source for use within the fully implantable systems described herein is a rechargeable battery. However, it is to be understood that other power sources may also be employed. For example, an ultracapacitor (also known as a supercapacitor) may be used. An ultracapacitor, like a conventional capacitor, allows an electric charge (voltage potential) to be stored therein. Unlike a regular capacitor, the energy density of the ultracapacitor is orders of magnitude greater than the energy density of a normal capacitor, thereby allowing a great amount of energy to be stored in the ultracapacitor. This stored energy may then be withdrawn from the ultracapacitor for subsequent use. Thus, for this type of application, where recharging must occur on a regular basis, and when appropriate discharge circuits are employed to control the rate of discharge or energy withdrawal, the ultracapacitor provides a viable alternative to a rechargeable battery for use within the implantable system.

In some embodiments of the present disclosure, a complete-in-canal (CIC) microphone 134 of the type described previously may be used to sense sounds and couple signals representative of such sounds to the speech and motion processor (SMP) circuits within its respective implantable portion.

It should be emphasized again that the partitioning illustrated in FIG. 1D, which shows that the ICVS and SMP circuitry are included within the first implantable unit 152, and which shows that the power source, e.g., rechargeable battery, is included within the second implantable unit 154, is only exemplary. In fact, in an exemplary embodiment, described below in connection with FIG. 1E, the SMP circuitry is included within the second implantable unit 162, leaving only the ICVS circuitry within the first implantable unit 112'.

The advantage of the wired system 150 shown in FIG. 1D is that a fully implantable system is provided wherein one of the two implantable units, e.g., the power unit 154, may be replaced, if necessary, through only minor surgery. As indicated, the cable 156 that connects the second unit 154 to the first unit 152 is detachable. The implantable connector that connects the cable 156 to the unit 154, may be of any suitable type, e.g., of the type commonly used with implantable pacemakers, or of the pressure type shown in U.S. Pat. No. 4,516,820 (Kuzma), incorporated herein by reference, or of the type shown in U.S. Pat. No. 4,495,917 (Byers), also incorporated herein by reference. Further, the first unit 152 may be connected with the second unit 154 without a connector, e.g., through an RF coil link connected to the first unit 152 that overlaps and is concentric with an RF coil of the second unit 154. This arrangement allows both the first unit 152 and second unit 154 to be controlled and powered via an external unit when needed.

The external headpiece 136 and external control unit 138, and programmer 108, may be used with the wired system embodiment 150 shown in FIG. 1D in the same manner as these components are used with the single unit embodiment 130 shown in FIG. 1C.

Figure 1E:
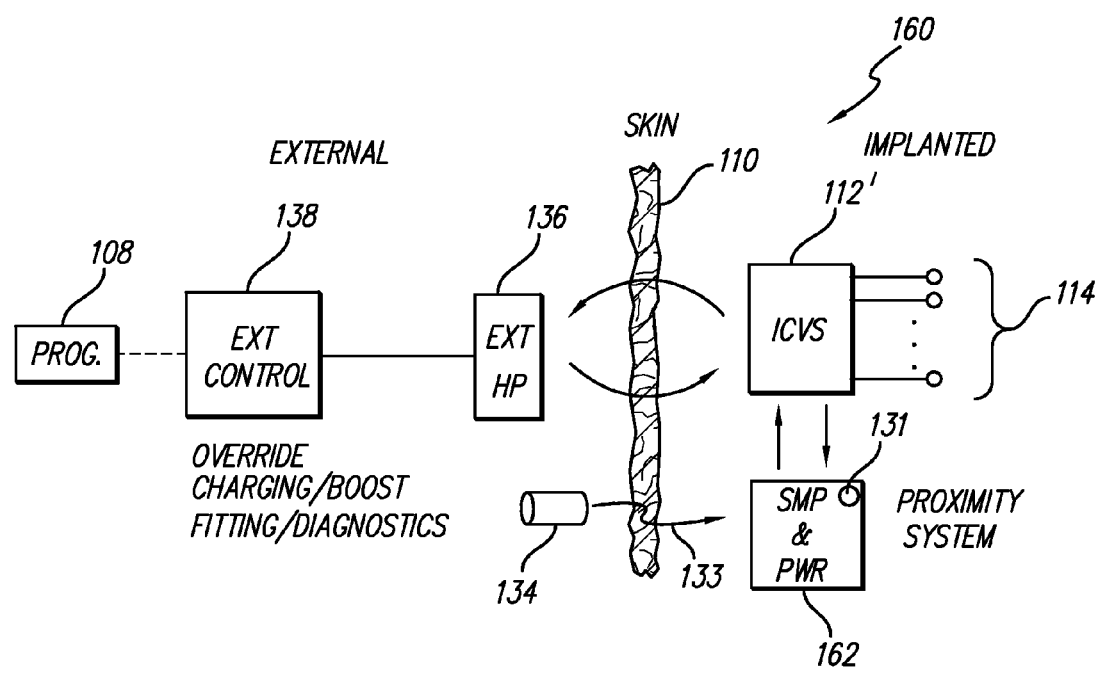
FIG. 1E shows another exemplary embodiment wherein a fully implantable, partitioned, proximity system is used.

Turning next to FIG. 1E, a partitioned proximity system 160 is shown that is similar to the wired system 150 shown in FIG. 1D, but without the use of a connecting cable 156 connected between the two units. As seen in FIG. 1E, a first implantable unit 112' comprises an ICVS with at least one electrode array 114 connected thereto. An advantage of the proximity system 160 is that the first implantable unit 112' may be substantially the same as, or identical to, that of the ICVS 112 used in existing cochlear stimulation systems (see FIG. 1A or FIG. 1B). This allows existing stimulation systems having an ICVS 112 to be upgraded to a fully implantable system as shown in FIG. 1E. A second implantable unit 162 includes speech and motion processor (SMP) circuits, motion sensors 131, and a power source, e.g., a rechargeable battery.

The second unit 162 is implanted so as to be in close proximity to the first unit 112'. As explained in more detail below, an exemplary configuration includes a two-conductor cable or lead having one end detachably connected to the unit 162 and having a coil attached at its other end and placed or positioned against or near the first unit 112' so as to be aligned with the coil included within the first unit 112'. An edge channel grove is formed around the periphery of the second unit 162, and provides a convenient channel into which the cable or lead may be wound, like the string of a yo-yo, as the second unit 162 is positioned adjacent the first unit 112'. This allows inductive coupling to occur between the implantable units 112' and 162 in the same manner as occurs between the BTE unit 120 and the ICVS 112 shown in FIG. 1B, or between the headpiece 106 and the ICVS 112 shown in FIG. 1A.

A suitable microphone, e.g., a complete-in-canal (CIC) microphone 134 of the type described previously, may be used to sense sounds (pressure waves) and couple electrical signals representative of such sounds to the speech and motion processor (SMP) circuits within the implantable portion 162. Alternatively, as described below, a suitable microphone may be fashioned as an integral part of the second unit 162.

The external headpiece 136 and external control unit 138, and programmer 108, may be used with the partitioned proximity system embodiment 160 shown in FIG. 1E in the same manner as used with the single unit embodiment 130 shown in FIG. 1C and the partitioned wired system embodiment 150 shown in FIG. 1D.

By using the system shown in FIG. 1E, it is seen that the following advantages are achieved: (1) older implants, i.e., existing implantable cochlear stimulation (ICS) units may be upgraded to fully implantable systems without replacing the implant ICS units and electrode(s) 114 simply by adding an implantable vestibular stimulation (IVS) unit with associated electrode(s) 114; (2) older implants, i.e., expired ICVS units 112 my be upgraded to fully implantable systems without replacing the implant ICVS and electrode(s) 114, (3) implantable systems may be upgraded with improved battery (or other power source) technology and lower-power more-sophisticated SMP circuits, as such become available, with only minor surgery for the patient; (4) an implanted package containing a motion sensor and vestibular stimulating electrodes may be appended to a previously implanted cochlear implant, and vice versa; (5) batteries can be replaced with only minor surgery, as required; and (6) charging, override, power boost, fitting and diagnostics may be performed by simply overriding the implanted SMP circuits with an external speech and motion processor.

A Fully Implantable Cochlear/Vestibular Implant System (FICVIS)

With the foregoing as a foundation for the principles practiced by the present disclosure, a more complete description of a fully implantable cochlear/vestibular implant system (FICVIS) will next be described. Three configurations or embodiments of such a FICVIS are respectively illustrated in FIGS. 2A, 2B and 2C; and functional block diagrams of the implantable stimulation systems 400 and 400' are illustrated in FIGS. 2D and 2E respectively. As seen in these figures, and particularly in FIG. 2D, the FICVIS comprises a modularized system that includes various combinations of at least three modules. The three modules include: (1) a small implantable cochlear/vestibular stimulator (ICVS) module 10, with permanently attached cochlear electrode array 12 and vestibular electrode array(s) 200; (2) an implanted speech and motion processor (ISMP) module 30, with integrated microphone 32, motion sensor(s) 201 (similar to sensors 131), and a rechargeable battery 34; and (3) an external module 50. In one embodiment, the external module 50 comprises an external speech and motion processor (ESMP) module. In another embodiment, the external module 50 comprises an external battery charger (EBC) module.

At the outset it should be noted that the present disclosure is not directed, per se, to the specific electronic circuitry or electronic components used or housed within each of these four modules. Any type of suitable circuitry could be used in the modules that perform the functions indicated. Circuitry and components suitable for these purposes is disclosed, e.g., in the referenced patents. The present disclosure, rather, is directed to a system that combines the indicated modules in a way that provides the advantages and benefits enumerated herein, which advantages and benefits have not heretofore been available.

As schematically seen best in FIG. 2D, the ICVS module 10 includes ICVS circuitry 14 hermetically sealed in compartment 15. Electrical feed-through pins ("feedthrus") 17 and 19 connect a coil 20 to the ICVS circuitry 14. The coil 20 is thus not housed within the hermetically sealed compartment 15, but is embedded within a suitable biocompatible substance 21, e.g., epoxy molding, which is affixed to the walls of the sealed compartment 15. Other feedthrus 22 and 202 electrically connect the electrode arrays 12 and 200 respectively to the ICVS circuitry 14 through a non-hermetic compartment 23, as explained more fully below in conjunction with FIG. 2D.

The electrode arrays 12 and 200 include a multiplicity of spaced-apart electrode contacts 13 at their distal ends, which electrode contacts are adapted to be placed inside of the cochlea and in the vestibular labyrinth or otherwise near neural vestibular tissue in order to provide an electrical stimulus to such tissue. A typical cochlear electrode array 12 may include, e.g., anywhere from 8 to 22 electrode contacts 13. A typical vestibular electrode array 200 may include, e.g., anywhere from 1 to 22 electrode contacts 13 at each of its (typically 3 to 5) ends 203.

In addition to the coil 20, which is connected to the feedthrus 17 and 19, one embodiment of the present disclosure utilizes a two-conductor lead 18 that is electrically connected in parallel with the coil 20. That is, one of the conductors of the lead 18, which may hereafter be referred to as a "pigtail" lead, is electrically connected to the feedthru 17, and the other of the conductors of the lead 18 is electrically connected to the feedthru 19. A jack 25, including, e.g., a tip electrode 24 (connected through one of the conductors of the lead 18 to the feedthru 17) and a ring electrode 26 (connected through the other of the conductors of the lead 18 to the feedthru 19), or other suitable electrode contacts, are located at a distal end of the lead 18.

Still referring to FIG. 2D, it is seen that the ISMP module 30 includes a hermetically sealed compartment 31 wherein ISMP and other electronic circuitry 33 (hereafter "ISMP circuitry" 33) is housed, along with a piezo-microphone 32, motion sensor(s) 201, and a rechargeable battery 34. Feedthrus 35 and 37 electrically connect the ISMP circuitry 33 to an electrical connector 36 formed in a suitable biocompatible material, e.g., epoxy molding, affixed to one side or edge of the ISMP module 30. Advantageously, the jack 25 at the distal end of the lead 18 may be detachably inserted into the connector 36. When thus inserted, the tip electrode 24 makes electrical contact through feedthru 35 with the ISMP circuitry 33, and the ring electrode 26 makes electrical contact through feedthru 37 with the ISMP circuitry 33. Those of skill in the art will readily recognize that this type of connector is similar to the basic connectors used in the pacemaker art in order to detachably connect a pacing lead to an implanted pacemaker. See, e.g., U.S. Pat. No. 4,764,132 (Stutz, Jr.) and the art cited therein.

One embodiment of the present disclosure includes the use of an RF lead 18' in place of the pigtail lead 18. As seen in FIG. 2D, the RF lead 18' has a jack 25' at one end having a tip electrode 24' and a ring electrode 26', adapted for insertion into the connector 36 of the ISMP module 30. At the other end of the lead 18' is an RF coil 20'. When used, the coil 20' of the RF lead 18' is positioned as close as possible to, and in alignment with, the coil 20 embedded within the molded epoxy 21 of the ICVS module 10.

As seen in FIG. 2D, both the ICVS module 10 and the ISMP module 30 are adapted to be implanted beneath the skin layer 110 of the patient. When the battery 34 has sufficient charge stored therein, the operation of the ICVS module 10 and ISMP module 30 proceeds without assistance from any external components. Thus, the system created by the ICVS module 10 and ISMP module 30 is self-sufficient, and truly becomes a fully implantable cochlear/vestibular implant system that provides the patient with auditory and vestibular sensation.

As needed, the fully implantable system may be assisted or boosted with an external module 50. Such external module 50 may be needed, e.g., to charge the battery 34, to transmit information from externally worn motion sensor(s) 204, or to override the ISMP circuitry 33 with external speech/motion processing controls and commands. Such external module 50 includes a headpiece 50', having a coil 52 therein. In some embodiments, the headpiece 50' may also include an external microphone. The headpiece 50' is connected to an external unit 54, which external unit comprises appropriate electronic circuitry, e.g., an external speech/motion processor (ESMP), an external battery charger (EBC), and/or external motion sensor(s) 204. The external unit 54, in turn, is powered from an external power source 56. Typically, the external power source will comprise a replaceable battery. However, the external power source could conceivably be any available power source, including batteries, including either replaceable or rechargeable batteries; charged super capacitors; DC power supplies connected to the AC line voltage (110 VAC, 60 Hz); solar panels; hand-operated generators; or the like.

Figure 2A:
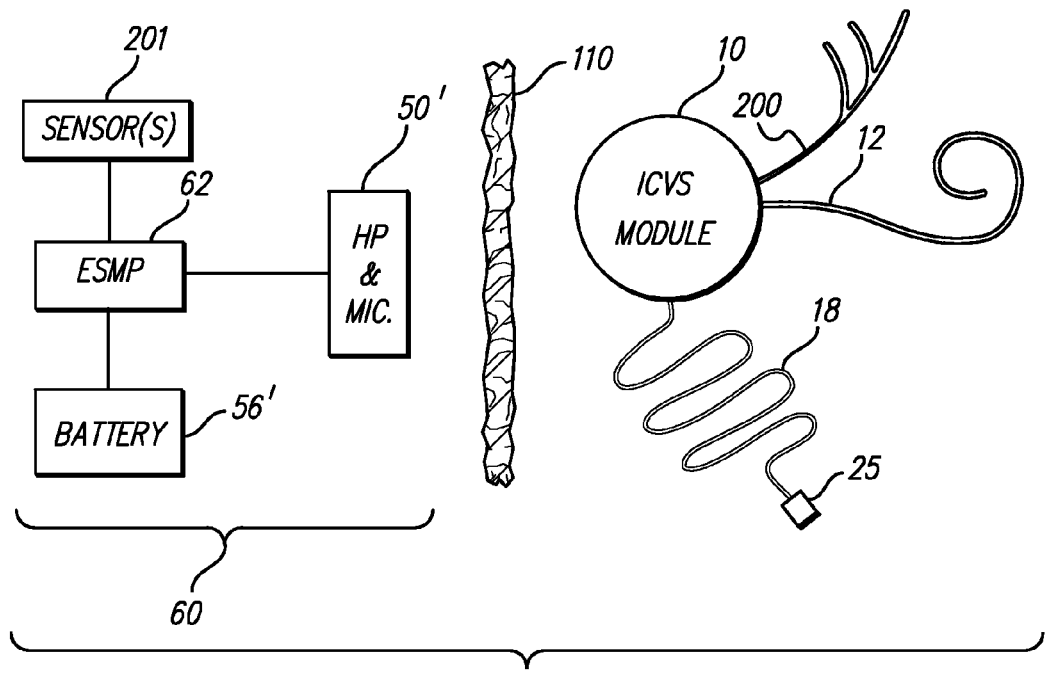
FIGS. 2A, 2B and 2C illustrate, respectively, three different exemplary configurations that may be realized using modularized fully implantable cochlear/vestibular implant systems (FICVIS)

FIG. 2A illustrates one variation of the teachings of the present disclosure that is particularly well suited for young children. This variation includes an ICVS module 10 used with an ESMP module 60. The ESMP module 60 includes a headpiece and microphone 50', a speech and motion processor 62 and related circuitry, and external motion sensor(s) 201, powered by a battery 56'. As such, the variation shown in FIG. 2A is similar to the system of, e.g., FIG. 1A. The configuration shown in FIG. 2A is especially suited for small children where the head size and bone thickness cannot accommodate the entire FICVIS system. The purpose of the configuration of FIG. 2A is to upgrade it to a fully implantable system once the patient has grown sufficiently so that the head size and bone thickness are no longer a limitation. An asymmetric array of magnets may be included in both the implanted portion and the external portion, so that constant relative orientation of the motion sensors and skull is maintained. Alternatively, the external motion sensors may be affixed rigidly to the skull via connection to a transcutaneous implanted osseointegrated fixture in the skull.

The advantage of the variation shown in FIG. 2A is that in can readily be upgraded to a fully implantable system at a later date by adding an ISMP module 30. The ISMP module 30 may be added using either of two approaches. In a first approach, an ICVS module 10 with pigtail lead 18 is first implanted, with the pigtail lead 18 not being used, as shown in FIG. 2A. That is, the jack 25 at the distal end of the pigtail lead 18 is not connected to anything when the ICVS module 10 is first implanted. Typically, the jack 25 will be protected with a suitable insulating protective cover or sleeve. Such unused pigtail lead 18 may, in some instances, be wrapped around a "dummy" ISMP module, which dummy ISMP module would preserve a space within the pocket formed under the skin for the later-implanted real ISMP module 30. In small children, however, such "dummy" module would likely not be used, but rather the pigtail lead 18, with protective sleeve, would simply be coiled under the skin in the region where the later-implanted ISMP module would eventually be located. Then, at a later date, when the ISMP module 30 is implanted, the pigtail lead 18 may be extracted through an incision, connected to a new ISMP module 30, and the ISMP module 30 could then be implanted, coiling the pigtail lead 18 around it, as described below.

In a second approach, the ICVS module 10, with or without a pigtail lead, is implanted first. Then, at a later date, when the ISMP module 30 is to be implanted, an incision is made next to the ICVS module 10 and a pocket is formed under the skin. An RF lead 18' (see FIG. 2D) is connected to the ISMP module 30 by way of the connector 36. The coil 26 at the other end of the RF lead 18' is pushed into the pocket and positioned adjacent to and aligned with the embedded RF coil 20 of the ICVS module 10. The ISMP module 30 is then inserted into the pocket with a rotation movement so as to wind the lead 18' around the edge of the module as it is inserted. An edge channel groove is provided around the periphery of the ISMP module 30 to facilitate this process. The incision that opens into the pocket is then closed with appropriate suturing or other means.

Figure 2B:
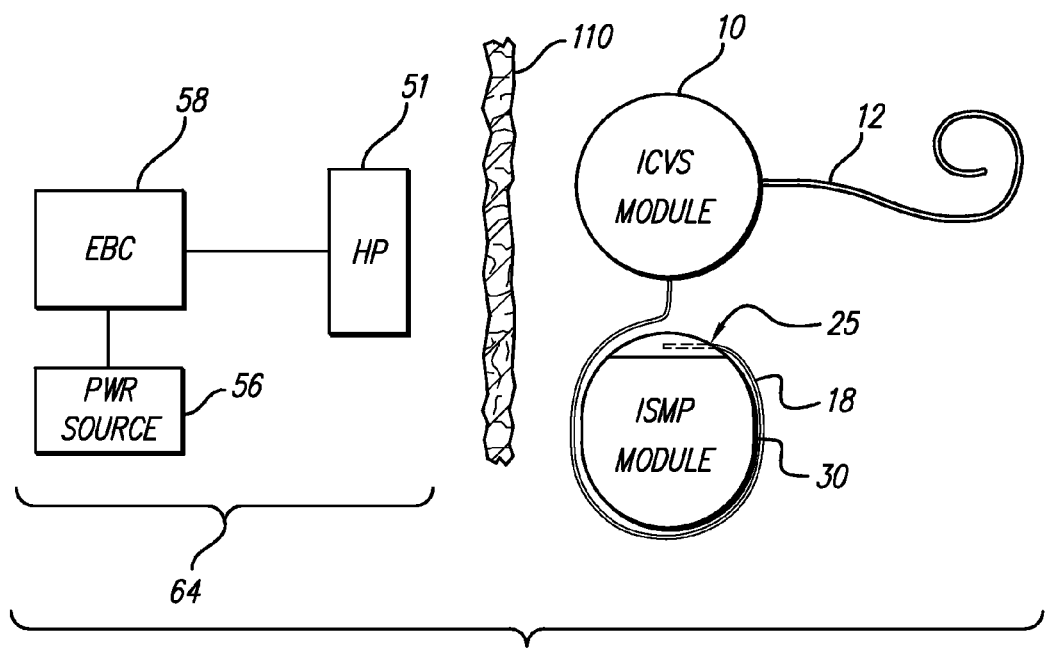

As seen in FIG. 2B, a second configuration of the present disclosure uses an ICVS module 10 with an ISMP module 30. The ISMP module 30 includes internal motion sensors or receives information from external motion sensors. Periodic recharging of the battery 34 within the ISMP module is performed using an external module 64 that includes a headpiece 51, an external battery charger (EBC) 58, and an external power source 56. The configuration shown in FIG. 2B represents a fully implantable system that is self-sufficient for as long as the battery 34 in the ISMP module remains charged. Typically, such battery 34 should last, under normal use, for at least two days. The battery 34, of course, requires periodic recharging, which recharging may preferably occur overnight during sleep using the EBC 58 and related components.

Figure 2C:
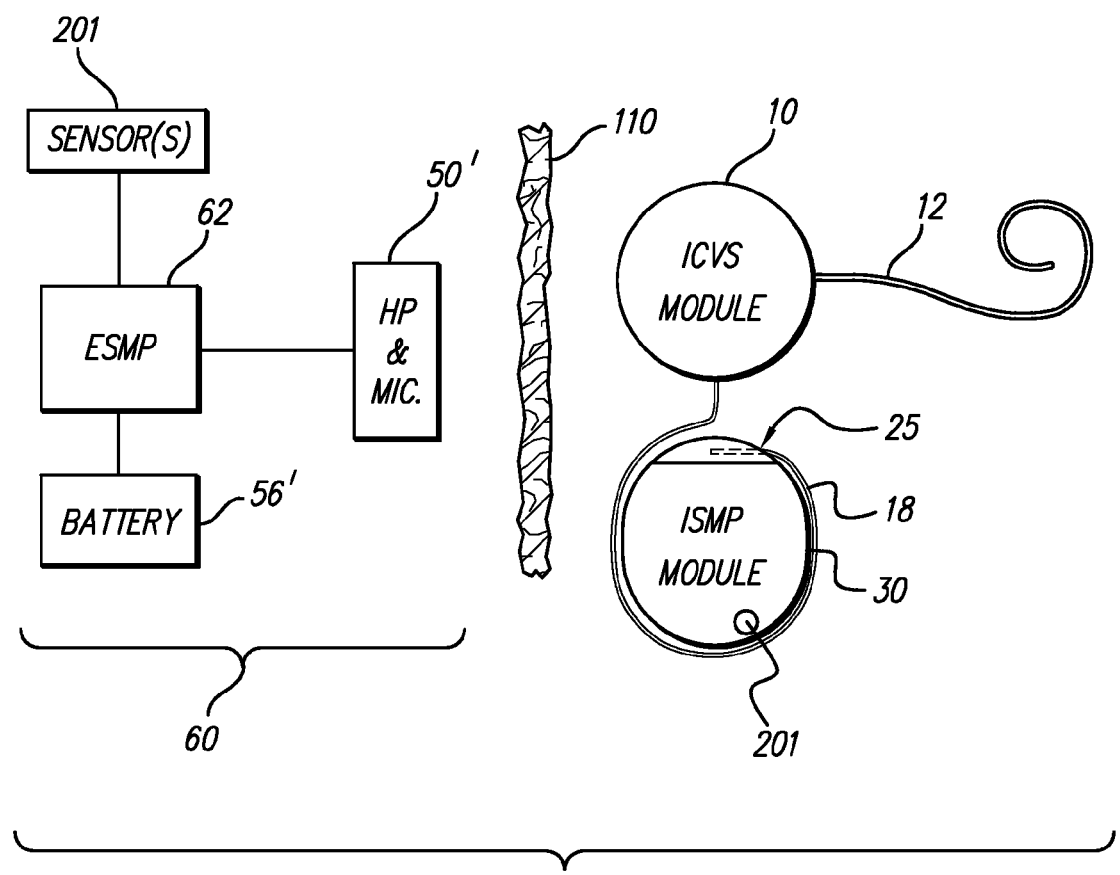
Figure 2D:
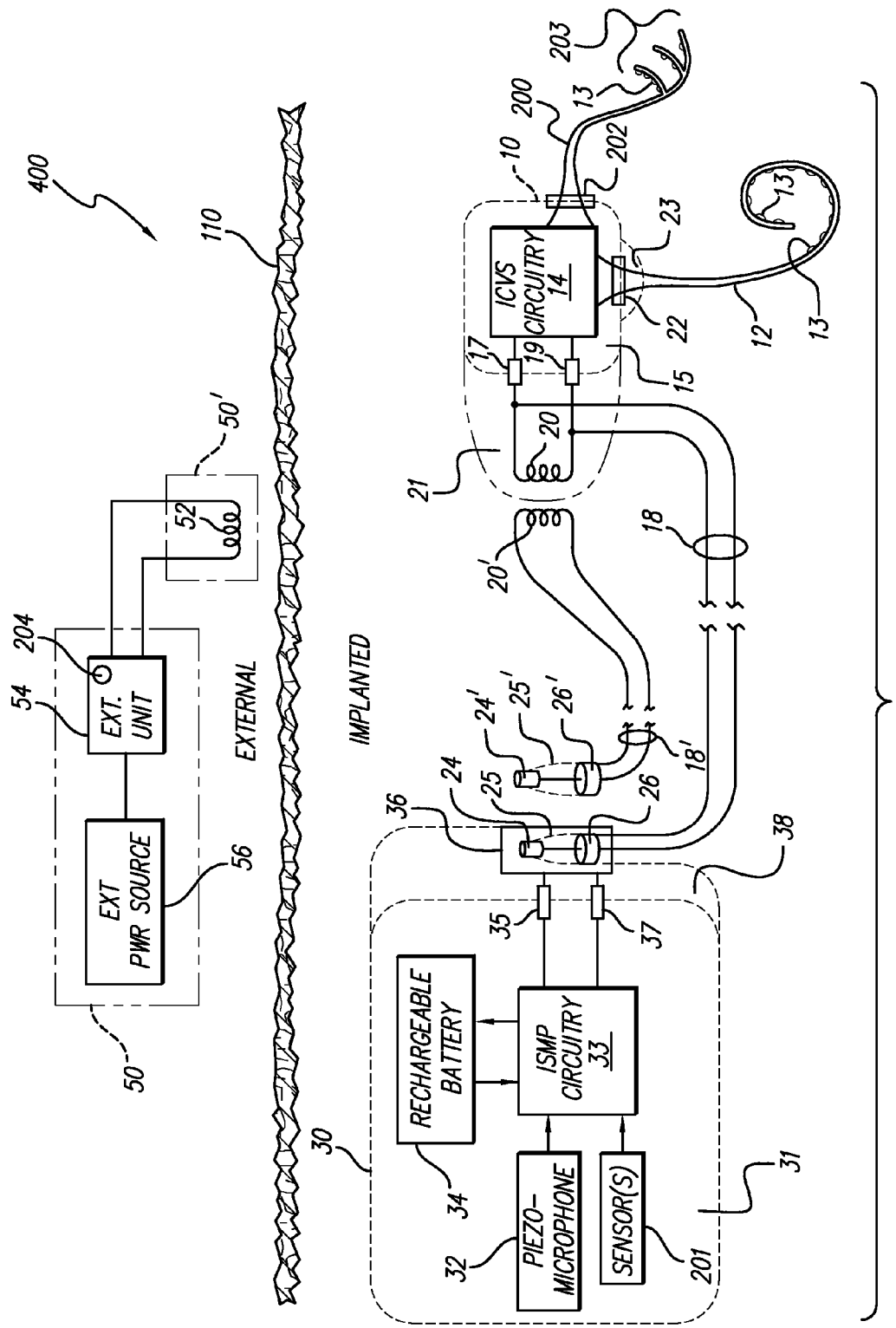
FIG. 2D is a schematic block diagram of a representative FICVIS that may be used by one or more embodiments of the disclosure.
Figure 2E:
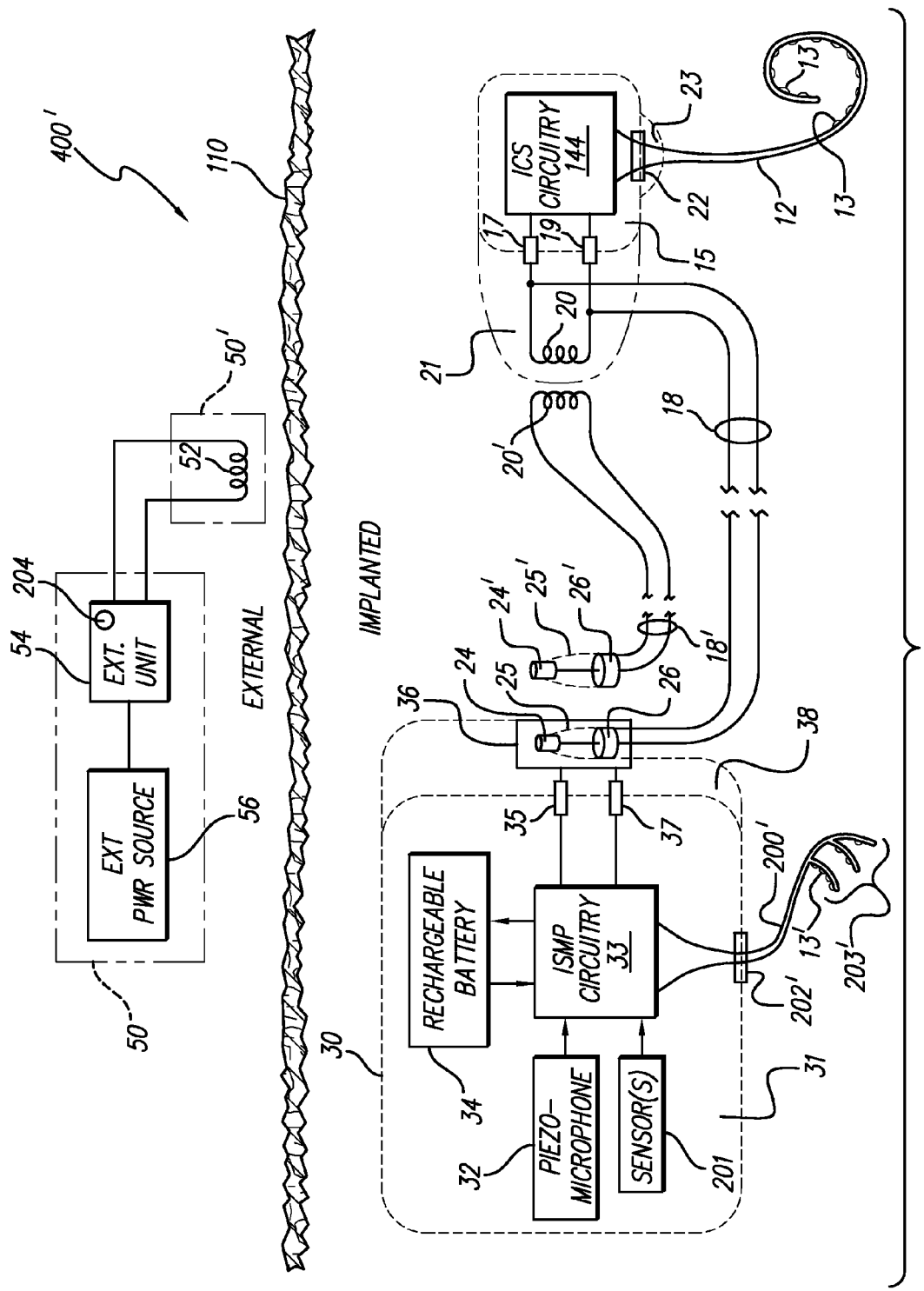
FIG. 2E is another schematic block diagram of a representative FICVIS that may be used by one or more embodiments of the disclosure.

Turning next to FIG. 2C, a third configuration of the present disclosure uses an ICVS module 10 with an ISMP module 30 with assistance from an external speech and motion processor (ESMP) module 60. The ESMP module 60 is essentially the same as that described above in connection with FIG. 2A. Such module 60 is used to drive (control) the ICVS module 10 and at the same time apply a slow charge to the implanted battery 34 contained within the ISMP module 30. The ESMP module 60 may be used jointly with the internal speech and motion processor 33 contained within the ISMP module 30, or alternatively to take over the function of the internal speech and motion processor should it malfunction or otherwise require replacement. External or internal motion sensors 201 provide motion information to the ESMP module 60 and ISMP module 30 as needed.

Another exemplary embodiment includes vestibular electrode array 200' electrically connected to the ISMP module 30 as shown in the implantable stimulation system 400' depicted in FIG. 2E, thus allowing subsequent implantation of vestibular sensors and stimulating electrodes in a patient previously implanted with a device that includes only the cochlear stimulator. The electrode array 200' would similarly include a multiplicity of spaced-apart electrode contacts 13' at its distal end, which electrode contacts are adapted to be placed in the vestibular labyrinth or otherwise near neural vestibular tissue in order to provide an electrical stimulus to such tissue. Similar to the vestibular electrode away 200, the vestibular electrode away 200' would also include, e.g., anywhere from 1 to 22 electrode contacts 13' at each of its (typically 3 to 5) ends 203'. Feedthru 202' electrically connects the electrode away 200' to the circuitry 33. In the embodiment shown in FIG. 2E, ICS circuitry 144 is used for the cochlear stimulation portion.

The mechanical construction of the various embodiments of the present disclosure are taught with reference to FIGS. 3A-7C of U.S. Pat. No. 6,272,382, (the '382 patent), previously incorporated herein by reference. The embodiments of the '382 patent need to be modified as described herein to include at least one additional lead with at least one electrode array (typically 3 to 5) extending from the body of the implant toward the vestibular system of a patient. Alternatively, the cochlear implant lead may be bifurcated to include a branch to the cochlea and a branch to the vestibular system. The branch to the vestibular system may in turn include further branches, as described herein with reference to FIG. 2D.

Most humans have two vestibular labyrinths, one in each ear that cooperate with each other to provide balance information to the central nervous system. The present disclosure may be practiced in a variety of bilateral embodiments with any other vestibular stimulation systems of the prior art or the present disclosure. The principles of such bilateral embodiments are exemplified by the teachings found in U.S. Pat. No. 6,546,291 (the '291 patent), previously incorporated herein by reference.

All of the speech and/or speech/motion processors of the present disclosure may be configured to provide auditory cues or feedback indicative of a patient's spatial orientation or velocity through the cochlear electrodes of the present disclosure. Such auditory feedback is described in further detail in the '046 and '149 patents, the teachings of which, as with the teachings of all other patents mentioned throughout this specification, are incorporated herein by reference.

As described above, it is thus seen that one or more embodiments of the present disclosure include a modular-based fully implantable cochlear/vestibular implant system (FICVIS). Such system advantageously is flexible in its application so as to meet the particular needs and wants of a given patient at a given time, including the ability to adapt to a range of head sizes and shapes.

As further described above, it is also seen that one or more embodiments of the present disclosure include such a modular-based FICVIS that offers a relatively simple and low-risk replacement surgery for its battery module, e.g., the ISMP module.

As additionally evident from the description above, it is seen that one or more embodiments of the present disclosure provide such a modular-based FICVIS that is highly reliable, exhibiting, e.g., life-time reliability for the ICVS module, cochlear electrode array, vestibular electrode array, and pigtail lead (when used), and further exhibiting a reliability of the ISMP module that is equal to or better than the maximum life of the battery used therein.

As described above, it is further seen that one or more embodiments of the present disclosure provide a hybrid cochlear/vestibular stimulation capable of simulating proper auditory and vestibular sensations to the brain of a patient. Thus, a patient using the present disclosure may benefit through the use of restored hearing and/or proper balance and orientation.

While the teachings of the present disclosure herein disclosed have been described by means of specific embodiments and applications thereof, numerous modifications and variations could be made thereto by those skilled in the art without departing from the scope of the invention set forth in the claims.

What is claimed is:

1. An implantable stimulation system, comprising:
    an implantable cochlear stimulator (ICS) having a pulse generator that generates electrical stimulation pulses as defined by control signals, a first lead having a plurality of electrodes thereon adapted to be inserted into a patient's cochlea, wherein electrical stimulation pulses are provided to the patient's auditory nerve as defined by the control signals;
    at least one microphone configured to sense and provide audio information;
    at least one motion sensor configured to sense and provide motion information; and
    a speech and motion processor (SMP) configured to generate the control signals in response to the audio and motion information provided by the at least one microphone and the at least one motion sensor, and to provide the control signals to the ICS,
    wherein the SMP further includes a second lead having at least one electrode thereon adapted to be inserted into the patient's semicircular canals or vestibule, or otherwise in proximity to the patient's vestibular nerve or its terminal branches, wherein electrical stimulation pulses are selectively provided to the vestibular nerve as defined by the control signals;
    wherein the SMP is dividable into a speech processing portion and a motion sensing portion, and wherein the speech processing portion of the SMP comprises an external portion, and wherein the motion sensing portion comprises an implantable portion, and further wherein the at least one motion sensor comprises an implantable motion sensor that is attached to the implantable portion of the SMP.

2. The implantable stimulation system of claim 1 wherein the at least one motion sensor is fixed relative to a patient's skull and generates motion information indicative of movement associated with the patient's skull.

3. The implantable stimulation system of claim 1 wherein both the ICS and the SMP are implantable.

4. The implantable stimulation system of claim 3 wherein the implantable ICS and SMP each further include an implantable coil, and wherein the system further includes:
    an external headpiece having an external coil adapted to be inductively coupled with the implantable coils, and
    an external control device coupled with the external headpiece, the external control device including circuits that include means for transmitting power and control signals to the implantable system through the inductively coupled external coil and implantable coils.

5. The implantable stimulation system of claim 4 wherein the at least one motion sensor is an implantable motion sensor that is coupled directly to the SMP.

6. The implantable stimulation system of claim 4 wherein the at least one motion sensor is an external motion sensor adapted to be fixed to the patient's skull and which is coupled to the SMP through a wireless link.

7. The implantable stimulation system of claim 4 wherein the at least one microphone comprises an external microphone coupled to the SMP through a wireless link.

8. The implantable stimulation system of claim 4 wherein the at least one microphone comprises an implantable microphone connected directly to the implantable SMP.

9. A method of stimulating the vestibular and cochlear nerves of a patient, comprising:
    implanting a pulse generator in a patient's head, the pulse generator having a first lead with at least one electrode thereon and a second lead with at least one electrode thereon, the pulse generator further having a return electrode, wherein the pulse generator selectively generates electrical stimulation pulses in response to control signals and applies those electrical stimulation pulses to the at least one electrode on the first lead or to the at least one electrode on the second lead, wherein the first lead is part of an implantable cochlear stimulator (ICS) module and the second lead is part of a speech and motion processor (SMP) module;
    inserting the first lead into the patient's cochlea and the second lead into the patient's semicircular canals, vestibule, or otherwise in proximity to the patient's vestibular nerve or its terminal branches, whereby electrical stimulation pulses are selectively provided to the cochlear or vestibular nerve as defined by the control signals;
    sensing sound waves through at least one microphone;
    sensing motion of the patient's head through at least one motion sensor mounted on or in the patient's head; and
    applying sensed sound and motion information to the SMP, wherein the SMP is configured to generate control signals responsive to sensed sound waves and sensed motion of the patient's head; and
    providing the control signals to the implanted pulse generator, whereby electrical stimulation is selectively provided to the patient's cochlear nerve in response to information sensed through the at least one microphone and electrical simulation is selectively provided to the patient's vestibular nerve in response to information sensed through the at least one motion sensor.

10. The method of claim 9 further comprising mounting the at least one motion sensor within the SMP module.

11. The method of claim 10 further comprising connecting the ICS module and the SMP module together using a cable link, wherein the ICS module and the SMP comprise separate implantable modules.

12. The method of claim 10 further comprising connecting the ICS module and the SMP together using a wireless link, wherein the ICS module and the SMP comprise separate implantable modules.

13. The method of claim 9 wherein sensing sound waves through the at least one microphone comprises using an external microphone coupled to the SMP through a wireless link.

14. The method of claim 9 wherein sensing sound waves through the at least one microphone comprises using an implantable microphone connected directly to the implantable SMP.

* * * * *